United States Patent
Kriesell et al.

(10) Patent No.: US 6,537,249 B2
(45) Date of Patent: Mar. 25, 2003

(54) MULTIPLE CANOPY

(75) Inventors: Marshall S. Kriesell, St. Paul, MN (US); Farhad Kazemzadeh, Bloomington, MN (US); Alan Langerud, Plymouth, MN (US)

(73) Assignee: Science, Incorporated, Bloomington, MN (US)

( * ) Notice: Subject to any disclaimer, the term of this patent is extended or adjusted under 35 U.S.C. 154(b) by 0 days.

(21) Appl. No.: 09/740,087

(22) Filed: Dec. 18, 2000

(65) Prior Publication Data

US 2002/0107480 A1 Aug. 8, 2002

(51) Int. Cl.[7] ............................................. A61M 37/00
(52) U.S. Cl. .................... 604/131; 604/151; 604/132; 128/288.01; 128/DIG. 12
(58) Field of Search .................. 604/131, 132, 604/151, 890.1; 128/DIG. 12, 288.01, 288.02, 288.03, 288.04

(56) References Cited

U.S. PATENT DOCUMENTS

| | | | | |
|---|---|---|---|---|
| 5,053,031 A | * | 10/1991 | Borsanyi | 128/DIG. 12 |
| 5,885,250 A | * | 3/1999 | Kriesel et al. | 604/132 |
| 5,925,017 A | * | 7/1999 | Kriesel et al. | 128/DIG. 12 |
| 5,957,891 A | * | 9/1999 | Kriesel et al. | 128/DIG. 12 |
| 6,068,613 A | * | 5/2000 | Kriesel et al. | 604/132 |
| 6,126,637 A | * | 10/2000 | Kriesel et al. | 604/132 |
| 6,174,300 B1 | * | 1/2001 | Kriesel et al. | 128/DIG. 12 |

* cited by examiner

*Primary Examiner*—Charles G. Freay
*Assistant Examiner*—John F. Belena
(74) *Attorney, Agent, or Firm*—Schwegman, Lundberg, Woessner & Kluth, P.A.

(57) ABSTRACT

A fluid delivery device having a self-contained stored energy membrane for expelling fluids at a precisely controlled rate, which is of a compact, laminate construction. The device is of very low profile so that it can conveniently be used for the precise delivery of a small volume of pharmaceutical fluids, such as insulin, morphine and the like, into an ambulatory patient at precisely controlled rates over extended periods of time. The device includes strategically configured, multiple fluid chambers to achieve the maximum possible average percent of extension of the membrane and thereby assure adequate fluid delivery pressure.

36 Claims, 10 Drawing Sheets

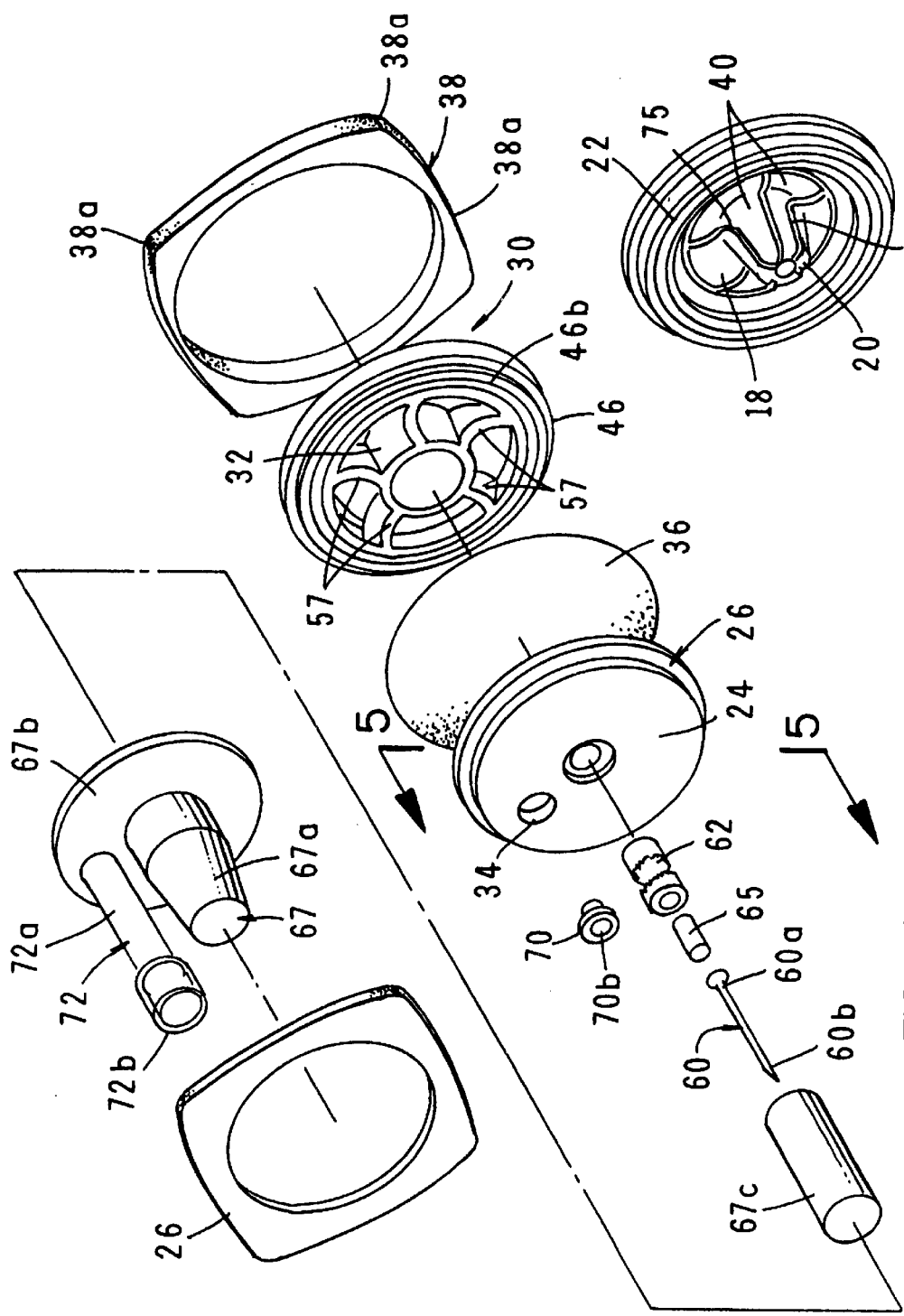

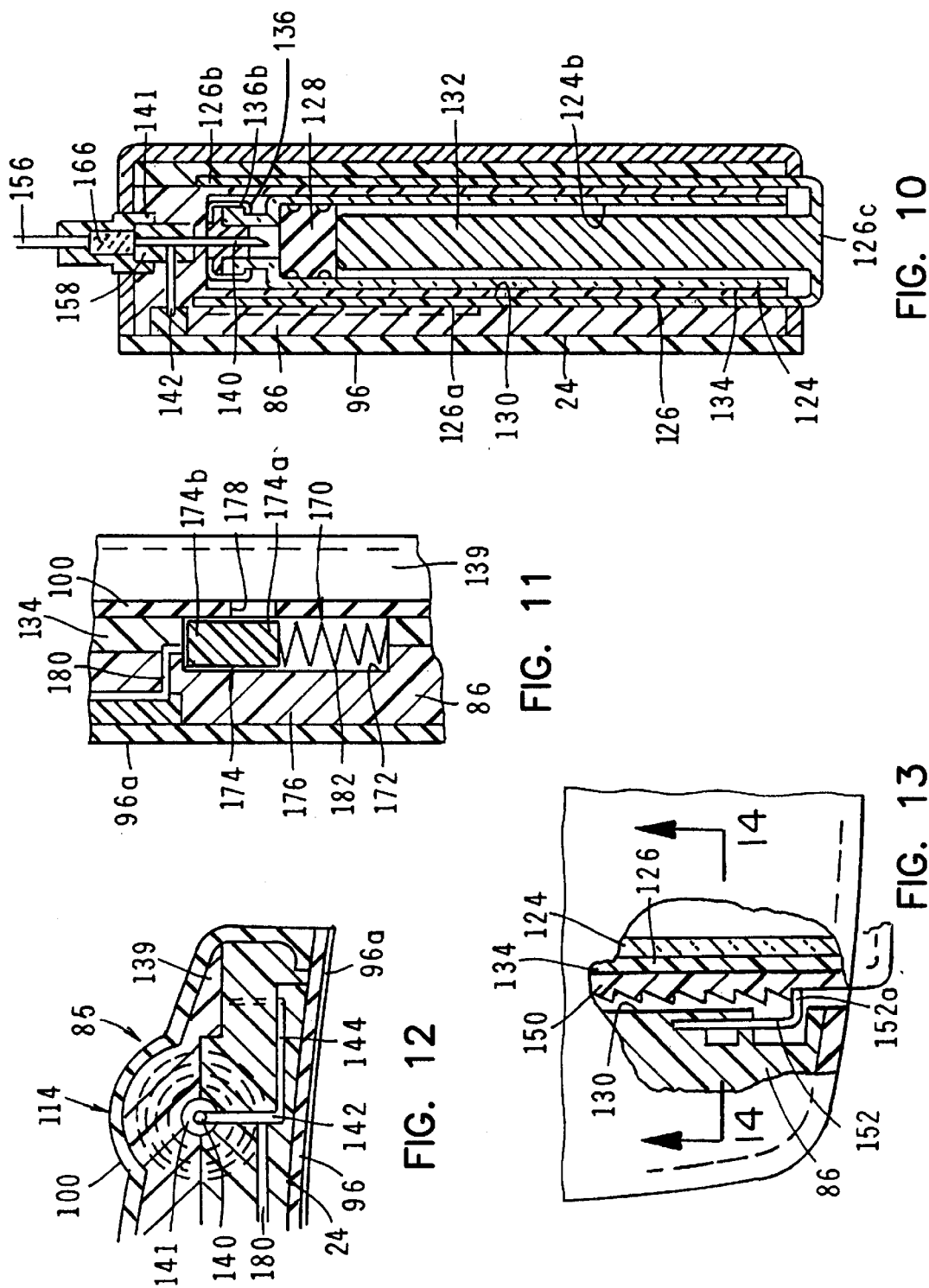

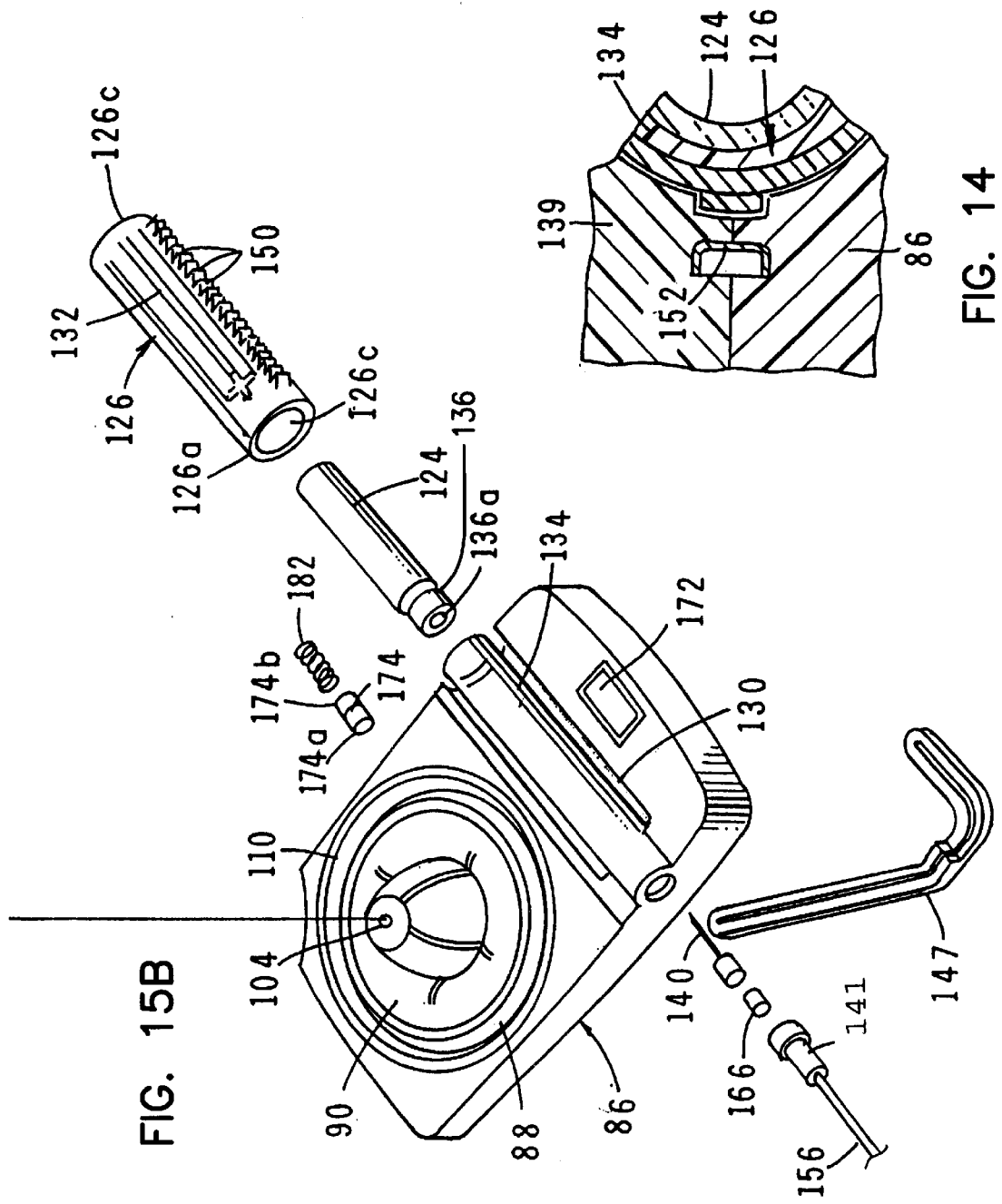

MULTIPLE CANOPY

BACKGROUND OF THE INVENTION

1. Field of the Invention

The present invention relates generally to fluid delivery devices. More particularly, the invention concerns an improved, ultra-low profile, multiple chamber fluid delivery apparatus for precise subdermal delivery over time of medicinal liquids to an ambulatory patient, the device including novel reservoir filling means.

2. Discussion of the Prior Art

A number of different types of liquid dispensers for dispensing medicaments to ambulatory patients have been suggested. Many of the devices seek either to improve or to replace the traditional hypodermic syringe that has been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night.

As will be appreciated from the discussion that follows, the low profile apparatus of the present invention is uniquely suited to provide precise fluid delivery management at a low cost in those cases where a variety of precise dosage schemes are of utmost importance.

An additional important feature of the apparatus of the present invention is the provision of a novel reservoir filling means disposed on the underside of the base.

Because the embodiments of the invention described herein comprise improvements to the devices described in U.S. Pat. No. 5,957,891 issued to Kriesel et al on Sep. 28, 1999, this patent is hereby incorporated by reference in its entirety as though fully set forth herein.

With regard to the prior art, one of the most versatile and unique fluid delivery apparatus was developed by Kriesel and described in U.S. Pat. No. 5,205,820. The components of this novel fluid delivery apparatus generally include: a base assembly, an elastomeric membrane serving as a stored energy means, fluid flow channels for filling and delivery, flow control means, a cover and an ullage which comprises a part of the base assembly. Another unique multiple chamber, reservoir type fluid delivery apparatus developed by Kriesel is described in U.S. Pat. No. 5,336,188. This novel fluid delivery apparatus includes, an elastomeric membrane that serves as a stored energy means and cooperates with the base of the apparatus to define a multi-part reservoir.

Another useful liquid delivery device is that described in U.S. Pat. No. 5,514,097 issued to Knauer. The Knauer device comprises a medicament injection apparatus for subcutaneous or intramuscular delivery of a medicament that conceals the infusion needle behind a needle shroud. On apparatus activation, the needle is thrust forward, pushing the needle tip outside the needle shroud with enough force to puncture the skin. The needle is thus automatically introduced into the tissue at the proper needle/skin orientation. In the same action, the apparatus automatically dispenses an accurate pre-set dose.

U.S. Pat. No. 5,226,896 issued to Harris also described a useful prior art device. This device comprises a multidose syringe having the same general appearance as a pen or mechanical pencil. The Harris device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel, ultra-low profile fluid delivery device having strategically configured, multiple fluid chambers and a unique filling means for filling the fluid chambers of the device.

SUMMARY OF THE INVENTION

It is an object of the present invention to provide an apparatus having a self-contained stored energy membrane for expelling fluids at a precisely controlled rate that is of a compact, laminate construction. More particularly, it is an object of the invention to provide such an apparatus which is of very low profile so that it can conveniently be used for the precise delivery of pharmaceutical fluids, such as endocrine type agents such as insulin, growth hormones and the like, into an ambulatory patient at controlled rates over extended periods of time.

It is another object of the invention to provide an apparatus of the aforementioned character that is highly reliable and very easy-to-use by lay persons in a non-hospital environment.

Another object of the invention is to provide an apparatus of the character described in the preceding paragraphs which includes novel reservoir filling means for conveniently filling the fluid reservoir of the device.

Another object of the invention is to provide an apparatus of the character described which includes a novel fill adapter which permits filling of the reservoir of the apparatus only with filling means of a specific construction, which is designed so that the fill adapter is irreversibly installed and, once installed, cannot be removed from the device housing.

Another object of the invention is to provide an apparatus such as that described in the preceding paragraph in which the reservoir fill means includes integrated structure to accept conventional prefilled pharmaceutical vials.

Another object of the invention is to provide an apparatus of the class described which further includes delivery means for precisely delivering medicinal fluids to the patient including the provision of a novel, dynamically mounted cannula assembly.

Another object of the invention is to provide an apparatus of the type described which includes indicator means for indicating fluid flow from the device reservoir.

Another object of the invention is to provide an apparatus of the character described which, due to its unique construction, can be manufactured inexpensively in large volume by automated machinery.

Other objects of the invention will become apparent from the discussion that follows.

BRIEF DESCRIPTION OF THE DRAWINGS

FIG. 3 is a cross-sectional view taken along lines 3—3 of FIG. 1.

FIG. 4 is a generally perspective, exploded view of the apparatus of the invention shown in FIGS. 1 and 2.

FIG. 5 is a view taken along lines 5—5 of FIG. 4.

FIG. 10 is a cross-sectional view taken along lines 10—10 of FIG. 8.

FIG. 11 is an enlarged, cross-sectional view taken along lines 11—11 of FIG. 8.

FIG. 12 is a cross-sectional view taken along lines 12—12 of FIG. 8 and rotated 180 degrees.

FIG. 13 is an enlarged, fragmentary view of the area designated in FIG. 8 by the numeral 13.

FIG. 14 is a cross-sectional view taken along lines 14—14 of FIG. 13.

FIGS. 15A, 15B are a generally perspective, exploded view of a portion of the embodiment of the invention shown in FIG. 7.

DESCRIPTION OF THE INVENTION

Figure 1:
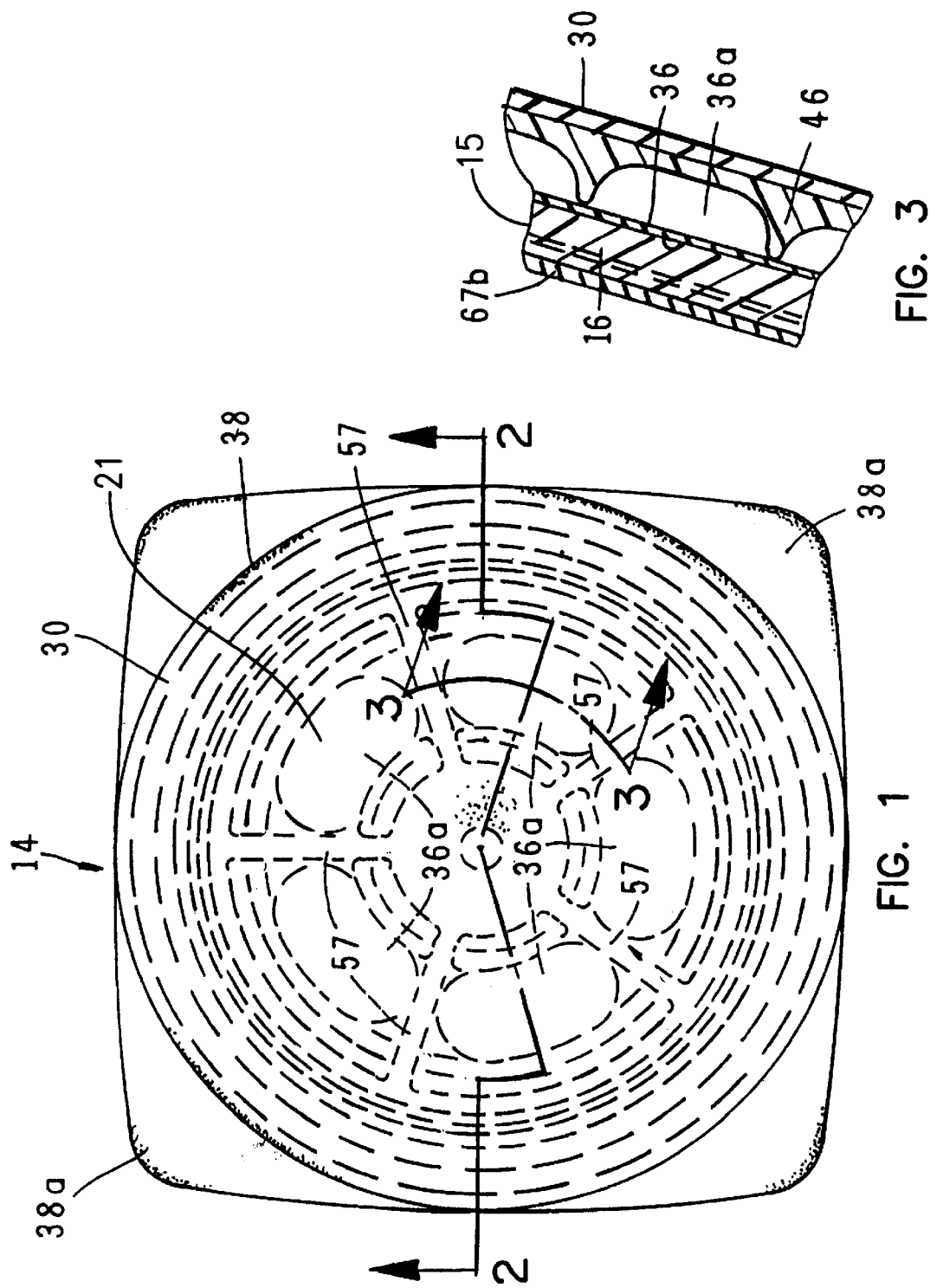
FIG. 1 is a top plan view of one form of the fluid delivery device of the present invention partly broken away to show internal construction.
Figure 2:
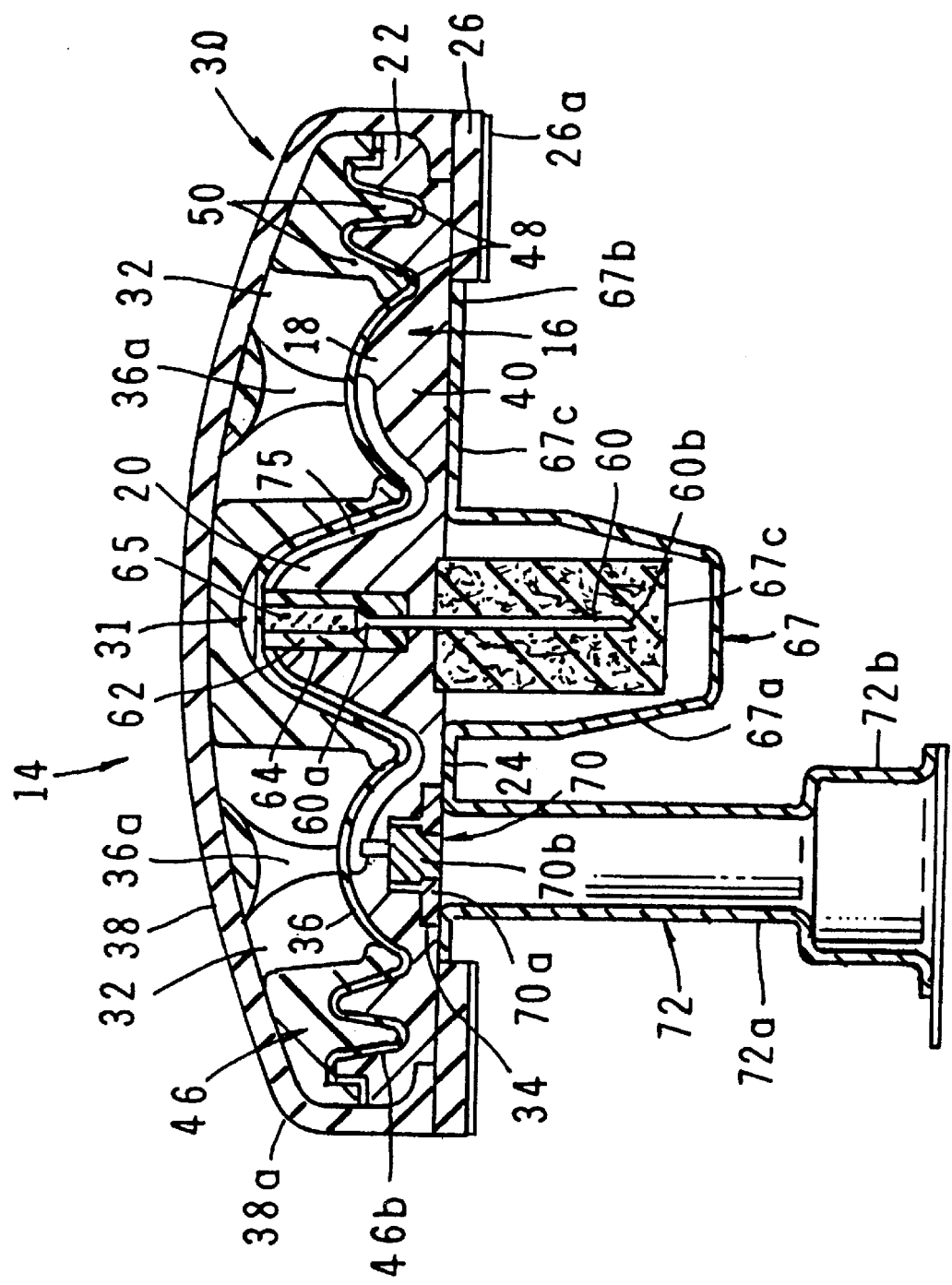
FIG. 2 is a cross-sectional view taken along lines 2—2 of FIG. 1.

Referring to the drawings and particularly to FIGS. 1 and 2, one form of the fluid delivery device of the invention is there shown and generally designated by the numeral 14. This form of the invention, which is specially designed for subdermal infusion of selected medicaments, comprises a housing 15 that includes a base 16 having an upper surface 18 including a generally dome shaped central portion 20 and a peripheral portion 22 circumscribing central portion 20. Base 16 also includes a lower surface 24 to which a patient interconnection means or adhesive pad 26 is connected. Pad 26 which comprises a foam tape having adhesive on both sides functions to releasably interconnect the device to the patient so as to hold it securely in place during the medicament delivery step. A peel-away member 26a covers a portion of the lower surface of the pad 26.

Figure 6:
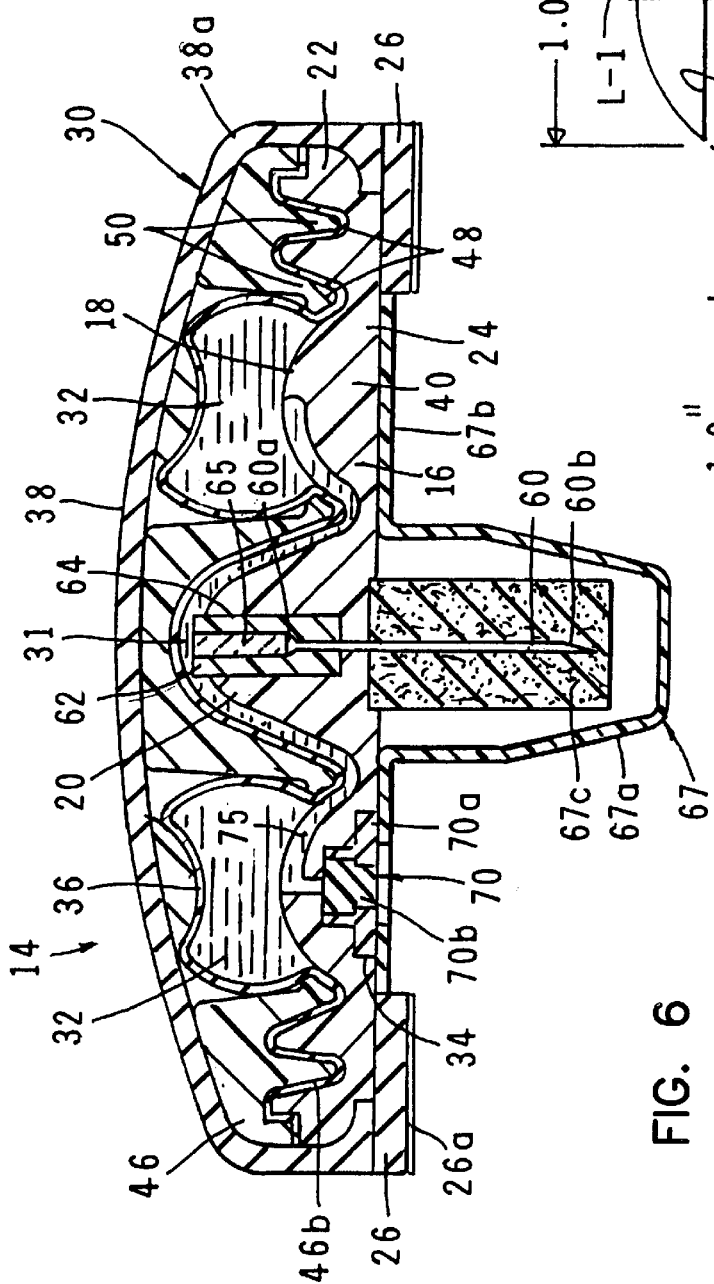
FIG. 6 is a side-elevational, cross-sectional view similar to FIG. 2, but showing the fluid chambers of the device filled with fluid.

A stored energy means cooperates with the upper surface 18 of base 16 and with uniquely configured cover means or cover assembly 30, to form a plurality of irregularly shaped fluid chambers 32 (FIG. 2). Base 16 has an inlet port assembly 34, that, in a manner presently to be described, is adapted to cooperate with a fill means for filling chambers 32 with the medicinal fluid to be infused into the patient. The stored energy means is here provided in the form of at least one distendable membrane 36 that is superimposed over base 16. Membrane 36 is distendable from the first position shown in FIG. 2 to the second position shown in FIG. 6 as a result of pressure imparted on the membrane by fluids introduced into the uniquely configured chambers 32 via inlet port assembly 34 (FIG. 2). As membrane 36 is distended into its second position in the manner shown in FIG. 6, internal stresses will be established, which stresses tend to move the membrane toward a less distended configuration and in a direction toward upper surface 18 of base 16. Membrane 36 can be constructed from a single membrane or from multiple membranes that are overlaid to form a laminate construction.

Provided within reservoir chambers 32 is ullage defining means for providing ullage within each of the chambers, which ullage means is engaged by membrane 36 as the membrane moves toward its less distended starting configuration. The ullage defining means here comprises the generally dome shaped, annular protuberance 40 formed on base 16. Ullage 40 circumscribes generally dome shaped protuberance 20 so that when the distendable membrane, after being distended, tends to return toward its less distended configuration, fluid contained within the fluid chambers 32 will flow outwardly toward the infusion means of the invention.

Superimposed over base 16 is the previously mentioned cover means, or cover assembly 30. Cover assembly 30 includes a rigid or semi-rigid cover portion 46 that functions, through the use of novel sealing means, to sealably enclose membrane 36 and a soft elastomer member 38 that overlays portion 46. The sealing means here comprises a pair of generally circular grooves 48 formed in peripheral portion of base 16 and a pair of cooperating, generally circular shaped rim like protuberances 50 formed on the peripheral lower surface 46b of the cover 46. Protuberances 50 are receivable within grooves 48 in the manner shown in FIGS. 2 and 6 and function to sealably clamp distendable membrane 36 between the cover portion 46 and base 16. Elastomer covering 38 forms the upper surface of the cover assembly and serves both to enclose chambers 32 and also to make the device more patient friendly. More specifically, as shown in FIGS. 1 and 4, member 38 includes soft edges and corners 38a that prevent the edges and corners of the device from causing unnecessary discomfort to the patient. Member 38 also includes a soft, pliable overcover that closes the fluid chamber 32. While several materials can be used for covering 38, materials such as a material sold under the name and style "Santoprene" by The Monsanto Company of St. Louis, Mo. has proven satisfactory for this purpose.

Examples of materials found particularly well suited for the construction of distendable membrane 36 include certain interpenetrating networks that can comprise silicone polymers silicone polymers. These materials are castable into thin film membranes and have high permeability that allows maximum transport of vapor and gas, high bond and tear strength, excellent low temperature flexibility, radiation resistance and exhibit generally flat stress-strain curves. Additionally, silicone elastomers retain their properties over a wide range of temperatures (−80° to 200° C.) are stable at high temperatures, and exhibit tensile strengths up to 2,000 lb./in² elongation up to 600%. Other suitable materials for construction of the stored energy membrane include natural and synthetic latex.

Manufacturers of materials suitable for use in construction of the distendable membrane include Dow Chemical, General Electric, B.P. Polymers, Mobay Chemical, Shell Oil Corp., Petrarch Systems, DuPont, Concept Polymers, Goodyear and Union Carbide Corp.

With respect to the structural cover 46 and base 16, these components can also be produced from a variety of materials including one of several polymer groups. The degree of hardness of these materials can range from soft, resilient or rigid, and the following readily commercially available polymers can be employed: Acrylics, polycarbonates, polypropylene (PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFE).

Figure 6A:
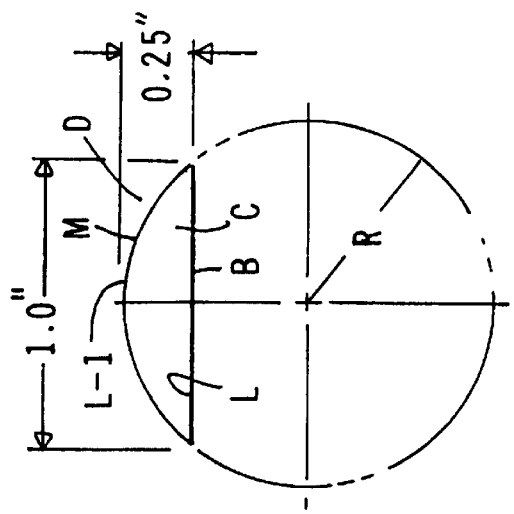
FIG. 6A is a diagrammatic view of an elastomeric membrane stretched into a generally dome shaped configuration.

The underlying objective of the present invention is to provide a very low profile patch-type of fluid delivery device that is capable of delivering approximately 1–10 cubic centimeters (cc) of fluid at a constant rate over a prescribed period of time. In the preferred form of the invention, the device uses the stored energy of an elastomeric membrane under tension as the source of pressure for fluid delivery. A linear rate of fluid delivery requires that a relatively constant level of chamber pressure be maintained during fluid delivery. The amount of pressure needed to perform this task is essentially small, however, an increase in the pressure level used is necessary to avoid interference from environmental factors such as shock, vibration, temperature variation or the like perturbations. The relationship of pressure (chamber) to membrane tension can be expressed as follows:

$$P = \frac{2T}{R}$$

Where P is equal to the chamber pressure, T is equal to the tension on the membrane and R is equal to the radius of the sphere, of which the arc formed by the inflated membrane is a part (see FIG. 6A). Tension T is calculated by the following:

T=Average % membrane extension times Modulus of elasticity of the membrane material times the Cross section of the area of extended membrane.

The average percent extension of the membrane is approximately equal to the ratio between the area of the membrane at rest (in the planar state) and the area of the membrane at extension. The modulus is a material specific parameter. In the following examples, it is assumed that the membrane used is an optimized material having, by way of example, a modulus of about 100 Lbs/in².

By way of a first example, a small single-chambered device such as that shown in FIG. 6A having a circular base B that is approximately 1 inch in diameter and a chamber height of 0.25 inch, could be used to demonstrate the performance factors of a simple stored energy membrane type design. The fluid chamber "C" in this example, whose approximate total volume is 1.7 cc, is a small fraction of a sphere whose radius R is 0.625 inch, a value that is relatively large. Filling of the reservoir causes the membrane "M" to extend from the position shown by the horizontal line L in FIG. 6A to the distended position indicated by the line L-1 as it expands upwards to fill the space allowed. This example yields a low average percent membrane extension of approximately 50%. If the average membrane extension is small and the resulting calculated membrane tension "T" is small, it follows that the pressure P will be very small. More particularly with extended membrane, the pressure P here equals:

$$\frac{2T}{R} \quad \text{or} \quad \frac{0.5}{0.625} = 3.2 \text{ psi}$$

While this pressure level could be used to deliver fluid from the chamber C, the linearity of the fluid delivery rate (flow volume over time) could be adversely affected by changes in environmental conditions such as the ambient temperature. In addition, it should be noted that the single reservoir design shown in FIG. 6A has a functional limit on fluid delivery that is dependent upon the height of the chamber. If the chamber height is decreased beyond a certain point, the average percent membrane extension will be insufficient to provide even the minimum chamber pressure for appropriate fluid delivery.

Figure 6B:
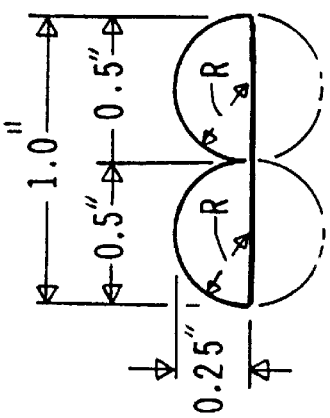
FIG. 6B is a diagrammatic view of an elastomeric membrane stretched into a pair of side-by-side, dome-shaped segments.

In the second example shown in FIG. 6B, the device membrane has been segregated by a canopy structure into two chambers, each with a base diameter of 0.5 inches and a height of 0.25 inches. Here the fluid volume accommodated by the two chambers would be approximately 2.14 cc. This increase in volume chamber for a same total base diameter of 1.0 inch is a significant advantage over the single chamber design of the first example. Further, the spheres, of which each chamber is a portion, have a radius R of 0.25 inches. The average percent of membrane extension in this example has increased to 100% and it is apparent that the resulting pressure P is significantly higher. More particularly, in this example where:

$$T = 1.25, \text{ the pressure } P = \frac{2T}{R} \quad \text{or} \quad \frac{2.50}{0.25} = 10 \text{ psi}$$

This significantly higher pressure is now within a pressure range that will deliver fluid at a rate that will not be adversely affected by changes in environmental perturbations conditions.

In the previous examples, a relatively wide tolerance bracket for the linearity of flow is assumed. If, however, the tolerance requirements for linearity of flow are tighter, the use of an ullage such as the protuberance 20 and 40 (FIG. 2) is required to prevent substantial tail off of the fluid delivery rate near the end of delivery cycle. The ullage volume required to maintain linearity of flow at a certain level is a function of the relationship between the radius of the chamber base and the height of the chamber as defined by the membrane in its extended state. This relationship is easiest to model if one assumes the chamber to be spherical in nature as has been assumed in the first and second examples.

Assuming that the delivery protocol requires that the linearity of flow rate be maintained within a 10% tolerance window, then the following could be said about the models described in the first and second examples. In the first example, the total volume of the chamber is approximately 1.74 cc. Maintaining a linearity of flow rate within 10% would require an ullage volume of 1.58 cc or 90% of the total chamber volume. This yields a delivery volume of only 0.16 cc, a volume substantially below the anticipated requirements. The total volume of the two chambers in the second example is approximately 2.14 cc. Here, an ullage volume of only 0.76cc would be required to deliver approximately 1.38 cc of fluid with a linearity of flow held to within 10% tolerance discounting other rate control and membrane tolerancing factors.

In the embodiment of the invention shown in FIGS. 1 through 6 of the drawings, the device membrane has been segregated by a novel canopy structure into five circumferentially shaped segments 36a that are permitted to extend into five circumferentially spaced, irregularly shaped chambers 32. As best seen in FIG. 2, each of the chambers 32 has a generally trapezoidal shape in cross section. As shown in FIG. 1, chambers 21 are separated by ribs 57 formed on cover 46. With the construction thus described and as illustrated in the drawings, the membrane 36 in its second extended position shown in FIG. 6 will have an average percentage stress well in excess of the 50% average percentage stress of the membrane "M" shown in FIG. 6A.

Referring particularly to FIGS. 2 and 3, the construction of an infusion means of the character described in the preceding paragraph, can be seen to include, in addition to the five chamber base and cover design, a downwardly extending hollow cannula 60 which is carried by a support member 62 that is received within a cavity 64 formed in base 16. Support member 62 also functions to support flow control means for controlling the rate of fluid flow from chamber 31 toward hollow cannula 60. This flow control means is here provided as a porous rate control frit 65 which can be constructed from a micro porous metal such as stainless steel. The frit can also be constructed from a porous ceramic or a porous plastic material.

Hollow cannula 60 has an inlet end 60a and an outlet end 60b formed in a needle-like segment that extends generally perpendicularly downward from the lower surface 24 of base 16. To protect cannula 60 from damage, a protective cover assembly 67 surrounds the cannula. At time of use the sheath portion 67a of the cover assembly can be broken away from the base portion 16. For this purpose, a serration line is preferably formed between the body of the sheath member and a connector collar 67b (FIG. 4) which functions to interconnect the cover assembly 67 with the base 16.

Referring particularly to FIGS. 2 and 4, one form of the novel filling means of the present invention is there illustrated. As previously mentioned, the filling means functions to controllably fill the various chambers 32 with the medicinal fluid which is to be infused into the patient. In the present form of the invention, the filling means comprises a septum assembly, a filling syringe assembly and a novel fill adapter assembly. As best seen in FIG. 2, septum assembly 70 is sealably disposed within the previously identified fill port 34 which is formed in base 16. Septum assembly 70 includes a septum housing 70a which is receivable within fill port 34 and an elastomeric pierceable core 70b that is sealably disposed within an opening formed in septum housing 70a.

As best seen in FIGS. 2 and 4, the fill adapter of the invention, that is generally identified by the numeral 72, is connected to connector collar 67b. Fill adapter 72 includes an upper wall portion 72a and an enlarged diameter lower wall portion 72b. Filling of the chambers 32 is accomplished using a conventional syringe having a cannula that is adapted to pierce core 70b. It is to be understood that the septum can be a slit septum and the syringe can have a blunt-end cannula.

In using the apparatus of the invention, after chambers 32 have been appropriately filled using a conventional syringe, the fill adapter is broken away from flange connector collar 67b along serration lines formed therein. Next cannula protective sheath 67a is removed as is a foam-like protector 67c that surrounds needle 60. This done, the device can be interconnected with the patient. This is accomplished by penetrating the patient's skin and tissue with the sharp point of the infusion cannula. During the infusion step, distended membrane 36 will urge the fluid contained within each of the chambers 31 and 32 to flow through flow passageways 75 formed in base 16 (FIG. 5) and into the inlet 60a of cannula 60 via the flow control means or rate control frit 65. Because of the novel configuration of chambers 32 and the cooperating stored energy means, the ultra-low profile device of the invention is capable of delivering the medicinal fluid to the patient at a precise rate over an extended period of time.

Turning next to FIGS. 7 through 15, an alternate form of the invention is there shown and generally designated by the numeral 84. This latter form of the invention, which is similar in some respects to the earlier described embodiment comprises a housing 85 that includes a base 86 having an upper surface 88 including a generally dome shaped central portion 90 and a peripheral portion 92 circumscribing central portion 90. Base 86 also includes a lower surface 24 to which a patient interconnection means or adhesive pad 96 is connected. Pad 96 which comprises a foam tape having adhesive on both sides functions to releasably interconnect the device to the patient so as to hold it securely in place during the medicament delivery step. A peel-away member 96a covers a portion of the lower surface of the pad 96.

Figure 9:
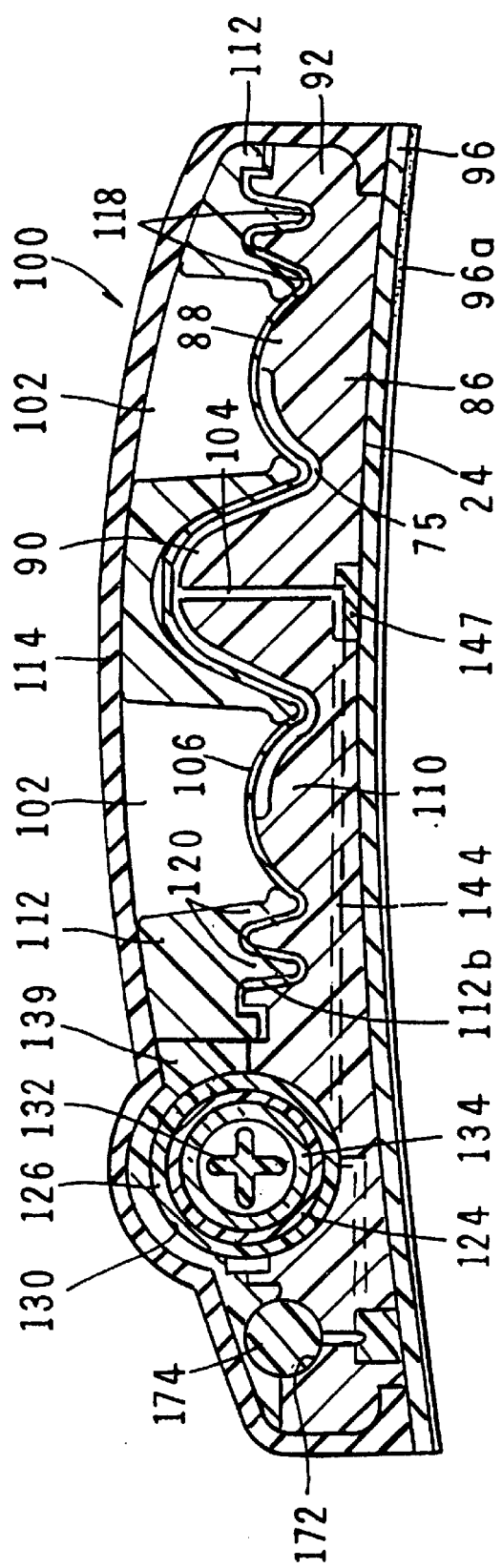
FIG. 9 is a cross-sectional view taken along lines 9—9 of FIG. 8.

As in the earlier described embodiment, a stored energy means cooperates with the upper surface 88 of base 86 and with uniquely configured cover means, or cover assembly 100, to form a plurality of irregularly shaped fluid chambers 102 (FIG. 9). Base 86 has an inlet-outlet flow passageway 104 that communicates with a novel fill means for filling chambers 102 with the medicinal fluid to be infused into the patient. The stored energy means is once again provided in the form of at least one distendable membrane 106 that superimposed over base 86. Membrane 106 is distendable from the first position shown in FIG. 9 to the second distended position as a result of pressure imparted on the membrane by fluids introduced into the uniquely configured chambers 102 via passageway 104. As membrane 106 is distended into its second position where it extends into chambers 102, internal stresses will be established, which stresses tend to move the membrane toward a less distended configuration and in a direction toward upper surface 88 of base 86. As before membrane 106 can be constructed from a single membrane or from multiple membranes that are overlaid to form a laminate construction.

Provided within reservoir chambers 102 is ullage defining means for providing ullage within each of the chambers, which ullage means is engaged by membrane 106 as the membrane moves toward its less distended starting configuration. The ullage defining means here comprises the generally dome shaped, annular protuberance 110 formed on base 86. Ullage 110 circumscribes generally dome shaped protuberance 90 so that when the distendable membrane, after being distended, tends to return toward its less distended configuration, fluid contained within the fluid chambers 102 will flow outwardly toward the infusion means of the invention.

Superimposed over base 86 is the previously mentioned cover means, or cover assembly 100. Cover assembly 100 includes a rigid or semi-ridge cover portion 112 that functions, through the use of novel sealing means, to sealably enclose membrane 106 and a soft elastomer member 114 that overlays portion 112. The sealing means here comprises a pair of generally circular grooves 118 formed in the peripheral portion of base 86 and a pair of cooperating, generally circular, annular shaped rim like protuberances 120 formed on the peripheral lower surface 112b of the cover 112. Protuberances 120 are receivable within grooves 118 in the manner shown in FIG. 9 and function to sealably clamp distendable membrane 106 between the cover portion 112 and base 86 thus forming a bonded, hermetically sealed assemblage. As before, elastomer covering 114 forms the upper surface of the cover assembly and serves both to enclose chambers 102 and also to make the device more patient friendly. The same materials identified in connection with the embodiment of the invention shown in FIGS. 1 through 6 are suitable for use in the construction of the cover assembly 100, the membrane 106 and the base 86.

Figure 15A:
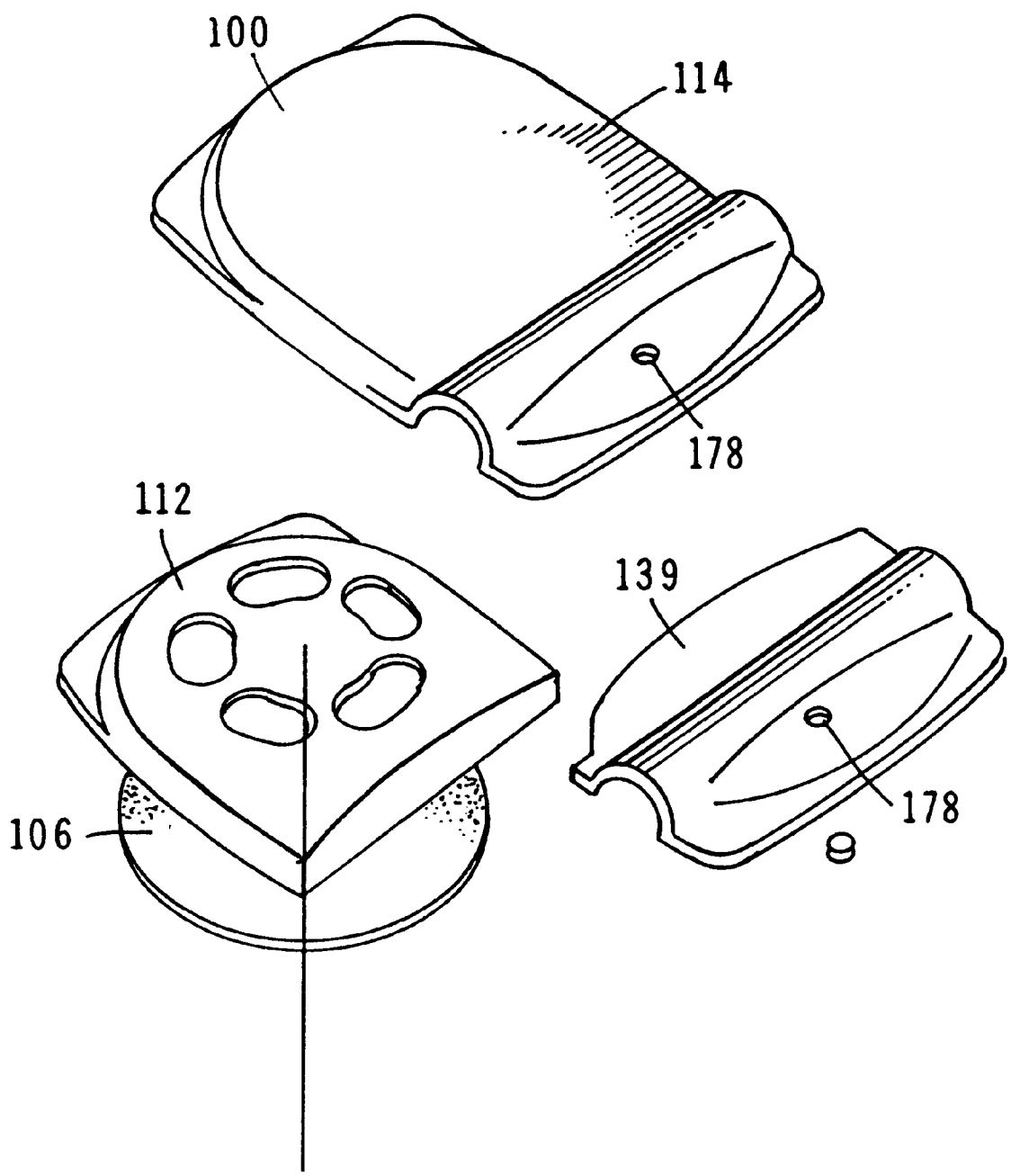

Considering next the novel fill means or fill assembly of the invention, this portion of the apparatus comprises a container subassembly 124, and an adapter subassembly 126 (FIG. 15). As best seen in FIG. 10, a plunger 128 is telescopically movable within chamber 124*b* of container subassembly 124 between first and second locations. As shown in FIGS. 10 and 15, adapter subassembly 126 comprises a hollow housing 126*a* having a first open end 126*b* and a second closed end 126*c*. The adapter subassembly 126 is telescopically receivable within an elongated receiving passageway 130 formed in housing 85 in the manner best seen in FIGS. 7, 9, and 10 so that the adapter subassembly can be moved from a first extended position shown in FIGS. 7 and 15B into the second fluid dispensing position shown in FIG. 10. Adapter subassembly 126 also includes pusher means shown here as an elongated pusher rod 132 that functions to move plunger 128 within the fluid chamber 124*b* of the container subassembly during the reservoir filling step.

As best seen in FIG. 9, disposed between the outer wall of container subassembly 124 and the inner wall of adapter 126 is a vial housing or receiving tube 134. With this construction, during the mating of the reservoir fill assembly with the base assembly, the outer wall of adapter subassembly 126 is closely received within the receiving chamber 130 of the housing and as the adapter subassembly is urged inwardly or forwardly of the device housing, and the vial housing tube 134 is received within the adapter assembly 126. It is to be observed that when the adapter assembly is originally mated with the device housing, the container subassembly 124 can be moved telescopically inwardly of vial housing tube 134 in a manner to move the vial septum 136*a* of a septum assembly 136, which includes a septum clamping ring 136*b*, into piercing engagement with a hollow cannula 140. In this regard, it should be noted that hollow cannula 140 is supported by a needle housing 141 and extends inwardly into receiving chamber 130 in the manner illustrated in FIG. 10. As best seen in FIGS. 9 and 15, a fill assembly cover 139, which forms a part of the cover assembly 100, covers the fill means.

Figure 8:
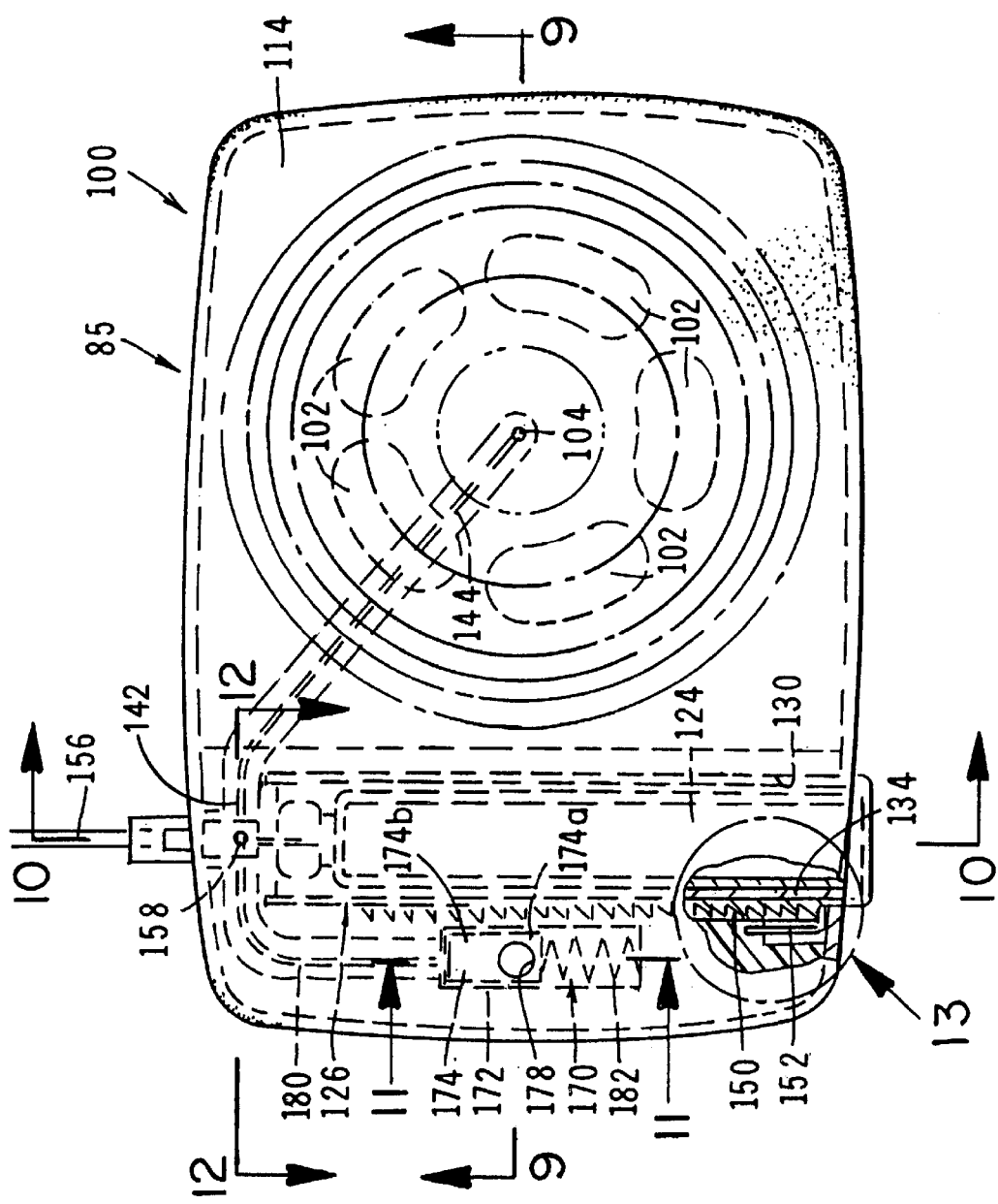
FIG. 8 is an enlarged, top plan view of the housing and fill means of the invention.

Once the fluid flow path between the hollow cannula 140 and the fluid reservoir of the apparatus is created via passageways 142, 144 and 104 (FIGS. 8, 9, and 12), an inward movement of the adapter subassembly can be accomplished by pushing on the closed end 126*c* thereof. As the adapter subassembly moves inwardly, pusher rod 132 will move plunger 128 forwardly of chamber 124*b*. As plunger 128 is moved forwardly, fluid contained within vial chamber 124*b* will flow through hollow cannula 140, into passageway 142 and finally into the fluid reservoir via passageways 144 and 104. As indicated in FIGS. 8, 9, and 15, passageway 144 is uniquely formed in a generally "L" shaped fluid flow plate 147 that is carried within base 86.

It is to be noted that adapter subassembly 126 is provided with a plurality of longitudinally spaced locking teeth 150 that slide under a resiliently deformable locking tab 152 during mating of the adapter subassembly with the device housing. Locking tab 152 is fixedly mounted on base 86 so that a leg 152*a* extends into receiving chamber 130 (FIG. 13). As the adapter subassembly is inserted into receiving chamber 130, leg 152*a* will deflect and slide over teeth 150. However, when the adapter subassembly is fully inserted as shown in FIG. 13, leg 152*a* will block removal of the adapter subassembly as well as the medicament vial of container subassembly 124.

Also forming an important feature of this latest form of the invention is the infusion means for controllably infusing the beneficial agents contained within the device reservoir into the patient. The infusion means here comprises an elongated delivery line 156 that is connected to housing 141 and communicates with the outlet passageway 158 of the device (FIG. 10) and a conventional line clamp 160 (FIG. 7A). Disposed between passageway 158 and line clamp 160 is a vent means shown here as a conventional gas vent and filter assembly 162 (FIG. 7A) which is also of the character previously described.

Also forming a part of the infusion means is a subcutaneous infusion needle assembly 164 that is connected to the distal end of delivery line 156. Assembly 164 can be of a readily commercially available type or alternatively can be of the character illustrated and described in U.S. Pat. No. 5,858,005 issued to the present inventor. U.S. Pat. No. 5,858,005 is incorporated by reference as though fully set forth herein. Reference should be made to this patent for a description of the construction and operation of one possible form of assembly 164.

Another feature of this latest form of the invention is the provision of flow rate control means for precisely controlling the rate of flow of the medicament to be infused from the device reservoir toward the infusion means described in the preceding paragraph. This rate control means here comprises a porous rate control frit 166 that is mounted within housing 85 between outlet passageway 158 (FIG. 10) that communicates with passageway 104 and delivery line 156. Frit 166 can be constructed from various materials of varying porosity, including by way of example, stainless steel, ceramic and porous plastics.

Figure 7B:
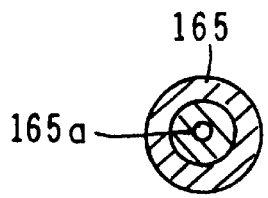
FIG. 7B is a greatly enlarged, cross-sectional view taken along lines 7B—7B of FIG. 7A.
Figure 7A:
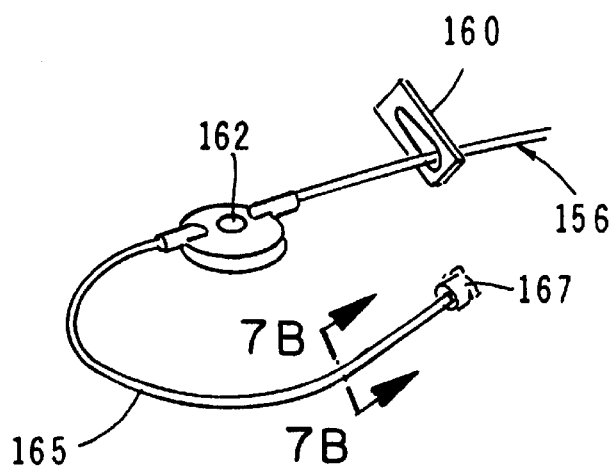
FIG. 7A is a generally perspective fragmentary view of another form of infusion means of the invention.
Figure 7:
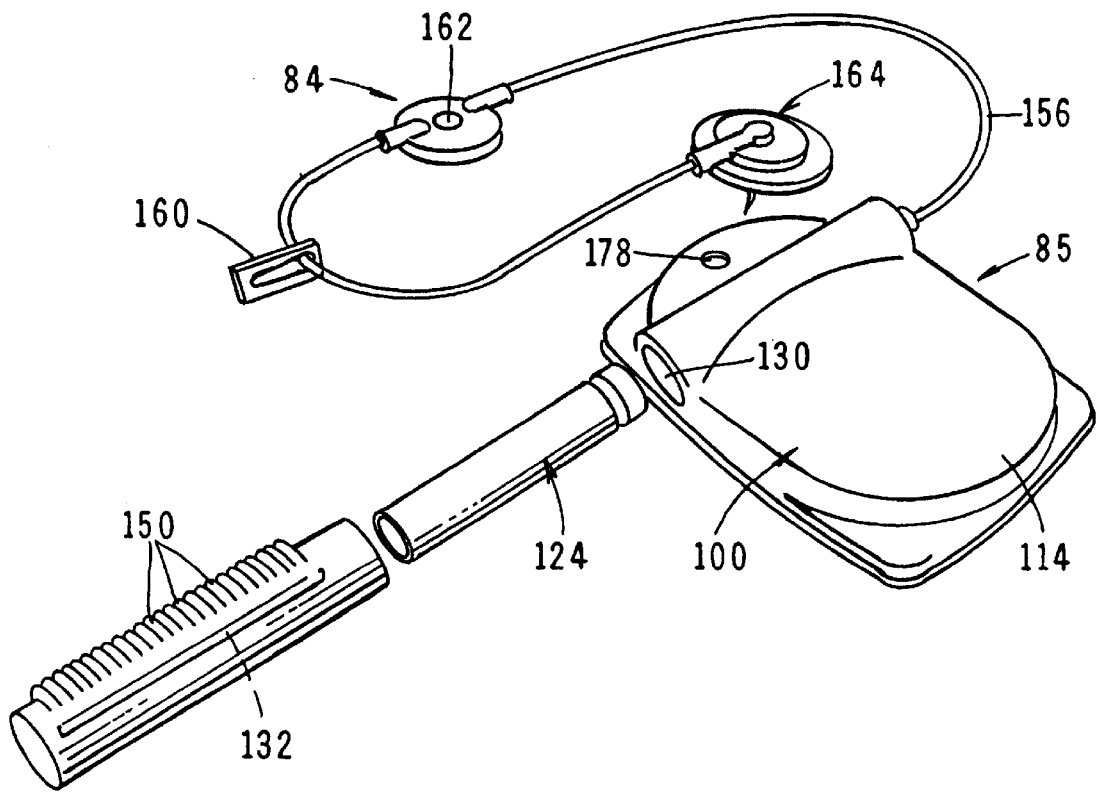
FIG. 7 is a generally perspective view of an alternate form of fluid delivery device of the invention.

Referring to FIGS. 7A and 7B, an alternate form of infusion means is there shown. This alternate embodiment includes rate control means provided in the form of an in line rate control capillary 165 having a coextended microbore 165*a* of a selected diameter (FIG. 7B) so as to precisely control the rate of fluid flow toward a luer connector 167 to which a needle assembly or the like can be connected. Rate control capillary 165 can be used separately or in series with rate control frit 166 to control the rate of fluid flow to the patient.

Still another important aspect of the apparatus of the invention is flow indicating means for visually indicating to the care giver that when clamp 160 is open fluid is flowing from the device reservoir toward the infusion means. In the present form of the invention this flow indicating means comprises a flow indicating assembly 170 that is disposed within housing 85 proximate receiving chamber 130. More particularly, flow indicating assembly 170 is housed within a hollow chamber 172 that is formed within base 86 and cover 139 (FIG. 9), and comprises a generally cylindrically shaped member 174 having a first segment 174*a* of a first color and a second segment 174*b* of a second color. Member 174 is sealably movable within chamber 172 in response to fluid introduced into the chamber under pressure via a fluid passageway 180. Biasing means, shown here as a coil spring 182, yieldably resists this movement of member 174 within chamber 172. In operation, when fluid is flowing from the reservoir of the device toward the infusion means via passageway 144, a portion of the fluid will be diverted into passageway 180 and will flow into chamber 172. When no fluid is flowing through passageway 180, segment 174a is viewable through viewing port 178. However, upon fluid flowing into chamber 172 via passageway 180, segment 174b will became visible through viewing port 178. For convenience, segment 174a may be colored red, while segment 174b may be colored green. Accordingly, when member 174 is displaced by fluid pressure flowing into passageway 180, the caregiver will see the green colored segment 174b indicating that fluid is flowing outwardly of the device. When fluid flow outwardly of the device ceases, fluid flow through passageway 180 will also cease. With no fluid flowing into chamber 172, spring 182 will urge member 174 into the starting position shown in FIG. 11 so that the red segment 174a is once again viewable through viewing port 178 thereby indicating to the caregiver that the device reservoir is empty.

Having now described the invention in detail in accordance with the requirements of the patent statues, those skilled in this art will have no difficulty in making changes and modifications in the individual parts or their relative assembly in order to meet specific requirements or condition. Such changes and modifications may be made without departing from the scope and spirit of the invention, as set forth in the following claims.

We claim:

1. A fluid delivery device for infusing medicinal fluids into a patient at a controlled rate comprising:
   (a) a housing including a base, a fluid inlet and a fluid outlet;
   (b) at least one extendable membrane connected to said base, said membrane being extendable from a first position proximate said base to a second distended position as a result of pressure imparted by fluids introduced into said fluid inlet to establish internal stresses tending to move said membrane toward said first position; and
   (c) a cover assembly connected to said base for forming in conjunction with said base and said membrane a plurality of circumferentially spaced, concentric chambers for receiving said membrane as said membrane extends toward said second extended position.

2. The delivery device as defined in claim 1 in which said base includes a central, upstanding protuberance and an upstanding protuberance spaced apart from and concentric with said central upstanding protuberance.

3. The device as defined in claim 1 in which each of said chambers is generally trapezoidal in cross section.

4. The device as defined in claim 1 in which the average percent of extension of said membrane in said second extended position is greater than fifty percent.

5. The device as defined in claim 1 in which the average percent of extension of said membrane in said second extended position is sufficient to provide a substantially linear delivery rate without interference from environmental factors.

6. The device as defined in claim 1 further including flow control means disposed between said inlet and said outlet for controlling fluid flow toward said outlet.

7. The device as defined in claim 1 further including infusion means for infusing the medicinal fluids into the patient, said infusion means comprises a fluid delivery line in communication with said outlet.

8. The device as defined in claim 1 in which said membrane cooperates with said base to form a fluid reservoir and in which the device further includes fill means for filling said reservoir.

9. The device as defined in claim 1 further including infusion means for infusing the medicinal fluids into the patient, said infusion means comprises a fluid delivery line in communication with said fluid outlet.

10. The device as defined in claim 1 further including flow indicating means carried by said housing for visually indicating that fluid is flowing toward the infusion means.

11. The device as defined in claim 1 in which said membrane cooperates with said base to form a fluid reservoir and in which the device further includes fill means for filling said reservoir, said fill means comprising a fill adapter connected to said base proximate said inlet and extending outwardly therefrom.

12. The device as defined in claim 1 in which said membrane cooperates with said base to form a fluid reservoir and in which the device further includes fill means for filling said reservoir, said fill means comprising a container subassembly connected to said housing.

13. The device as defined in claim 1 in which said container subassembly comprises:
   a. a container having a fluid chamber; and
   b. displacement means movable relative to said fluid chamber for expelling fluid from said fluid chamber.

14. A fluid delivery device for infusing medicinal fluids into a patient at a controlled rate comprising:
   (a) a housing having a base, a fluid inlet and a fluid outlet;
   (b) at least one extendable membrane connected to said base, said membrane being extendable from a first position proximate said base to a second distended position as a result of pressure imparted by fluids introduced into said fluid inlet to establish internal stresses tending to move said membrane toward said first position, said membrane cooperating with said base to define a plurality of spaced-apart, concentric fluid reservoirs
   (c) a cover assembly connected to said base for forming in conjunction with said base and said membrane a plurality of spaced-apart, concentric chambers for receiving said membrane as said membrane extends toward said second distended position;
   (d) fill means connected to said housing for filling said reservoir; and
   (e) infusion means connected to said housing for infusing the medicinal fluids into the patient.

15. The delivery device as defined in claim 14 including ullage means disposed within said reservoirs for providing ullage within said reservoirs.

16. The delivery device as defined in claim 14 in which said base includes a central, upstanding protuberance and an annular shaped, upstanding protuberance spaced apart from and concentric with said central upstanding protuberance.

17. The device as defined in claim 14 in which each of said chambers is generally trapezoidal in cross section and in which the average percent of extension of said membrane in said second distended position is greater than fifty percent.

18. The device as defined in claim 14 in which said infusion means comprises a fluid delivery line in communication with said outlet and an infusion needle assembly connected to said fluid delivery line.

19. The device as defined in claim 14 in which said fill means comprises a fill adapter connected to said base proximate said inlet and extending outwardly therefrom.

20. The device as defined in claim 14 in which said fill means comprises a container subassembly connected to said housing.

21. The device as defined in claim 20 in which said container subassembly comprises:
   (a) a container having a fluid chamber; and
   (b) displacement means movable relative to said fluid chamber for expelling fluid from said fluid chamber.

22. A fluid delivery device for infusing medicinal fluids into a patient at a controlled rate comprising:
   (a) a housing having a base, a fluid inlet and a fluid outlet, said base having a central, upstanding protuberance and an annular shaped, upstanding protuberance spaced apart from and concentric with said central upstanding protuberance;
   (b) at least one extendable membrane connected to said base, said membrane being extended from a first position proximate said base to a second distended position as a result of pressure imparted by fluids introduced into said fluid inlet to establish internal stresses tending to move said membrane toward said first position, said membrane cooperating with said base to define a fluid reservoir comprising a plurality of circumferentially spaced, concentric portions;
   (c) a cover assembly connected to said base for forming in conjunction with said base and said membrane a plurality of circumferentially spaced, concentric chambers for receiving said membrane as said membrane distends toward said second distended position;
   (d) fill means connected to said housing for filling said reservoir; and
   (e) infusion means connected to said housing for infusing the medicinal fluids into the patient.

23. The delivery device as defined in claim 22 in which said infusion means comprises a cannula connected to and extending from said base proximate said outlet.

24. The device as defined in claim 22 in which said infusion means comprises a fluid delivery line in communication with said outlet and an infusion needle assembly connected to said fluid delivery line.

25. The device as defined in claim 22 in which each of said chambers is generally trapezoidal in cross section.

26. The device as defined in claim 22 in which said cover assembly includes a soft, pliable elastomeric overcover.

27. The device as defined in claim 22 in which said fill means comprises a container subassembly connected to said housing said container subassembly comprising:
   (a) a container having a fluid chamber; and
   (b) displacement means movable relative to said fluid chamber for expelling fluid from said fluid chamber.

28. The device as defined in claim 22 in which said base includes a fill port and in which said fill means comprises a septum assembly connected to said fill port of said base.

29. The device as defined in claim 28 in which said septum assembly comprises a septum housing receivable within said fill port of said base and a septum sealably disposed within said septum housing.

30. A fluid delivery device for infusing medicinal fluids into a patient at a controlled rate comprising:
   (a) a housing including a base having a first, upstanding protuberance and a second upstanding protuberance spaced apart from said first upstanding protuberance;
   (b) stored energy means for forming, in conjunction with said base, a reservoir having an inlet port and an outlet port, said stored energy means comprising at least one distendable membrane superimposed over said base, said membrane being distendable as a result of pressure imparted by fluids introduced into said reservoir to establish internal stresses, said stresses tending to move said membrane toward a less distended configuration;
   (c) a cover assembly connected to said base for forming in conjunction with said base and said membrane a plurality of spaced-apart apertures for receiving said membrane as said membrane is distended;
   (d) filling means connected to said base for filling said reservoir
   (e) infusion means connected to said base for infusing medicinal fluids from said fluid reservoir into the patient, said infusion means comprising a hollow cannula having an inlet in communication with said outlet port of said reservoir; and
   (f) flow indicating means carried by said housing for visually indicating that fluid is flowing from the reservoir toward said infusion means.

31. The device as defined in claim 30 in which each of said chambers is generally trapezoidal in cross section, and in which the average percent of stretch of said membrane in said second distended position is greater than fifty percent.

32. The device as defined in claim 30 in which said cover includes a viewing port and in which said flow indicating means comprises a flow indicating assembly disposed within said housing, said indicating assembly comprising a reciprocally movable member that is viewable through said viewing port.

33. A fluid delivery device for infusing medicinal fluids into a patient at a controlled rate comprising:
   (a) a housing including a base having a first, upstanding protuberance and a second upstanding protuberance spaced apart from said first upstanding protuberance;
   (b) stored energy means for forming, in conjunction with said base, a reservoir having an inlet port and an outlet port, said stored energy means comprising at least one distendable membrane superimposed over said base, said membrane being distendable as a result of pressure imparted by fluids introduced into said reservoir to establish internal stresses, said stresses tending to move said membrane toward a less distended configuration;
   (c) a cover assembly connected to said base for forming in conjunction with said base and said membrane a plurality of spaced-apart apertures for receiving said membrane as said membrane is distended;
   (d) rate control means connected to said housing for controlling the rate of fluid toward the patient; and
   (e) infusion means connected to said base for infusing medicinal fluids from said fluid reservoir into the patient.

34. The device as defined in claim 33 in which said rate control means comprises a porous frit carried by said base.

35. The device as defined in claim 33 in which said infusion means comprises a delivery line connected to said housing and in which said rate control means comprises a capillary having a microbore disposed within said delivery line.

36. The device as defined in claim 33 further including fill means connected to said housing for filling said reservoir.

* * * * *